United States Patent [19]

Sih

[11] 4,188,481
[45] Feb. 12, 1980

[54] PYRAN ANALOGS OF 2,3,4,5-TETRADEHYDRO-PGI$_1$ COMPOUNDS

[75] Inventor: John C. Sih, Kalamazoo Township, Kalamazoo County, Mich.

[73] Assignee: The Upjohn Company, Kalamazoo, Mich.

[21] Appl. No.: 904,190

[22] Filed: May 8, 1978

Related U.S. Application Data

[63] Continuation-in-part of Ser. No. 821,541, Aug. 3, 1977, Pat. No. 4,109,082.

[51] Int. Cl.$^2$ ............................................. C07D 311/94

[52] U.S. Cl. .................................... 542/426; 542/429; 260/345.2

[58] Field of Search ....................... 260/345.2, 346.22; 542/426, 429

[56] References Cited

PUBLICATIONS

Johnson et al., Prostaglandins, 12, 915 (1976).

Primary Examiner—Nicky Chan
Attorney, Agent, or Firm—Robert A. Armitage

[57] ABSTRACT

This invention relates to pyran analogs of 2,3,4,5-tetradehydro-PGI$_1$ compounds. These novel prostacyclin-type compounds are useful for pharmacological purposes.

79 Claims, No Drawings

PYRAN ANALOGS OF 2,3,4,5-TETRADEHYDRO-PGI$_1$ COMPOUNDS

CROSS REFERENCE TO RELATED APPLICATION

This application is a continuation-in-part of Ser. No. 821,541, filed Aug. 3, 1977, now U.S. Pat. No. 4,109,082.

The present invention relates to pyran analogs of 2,3,4,5-tetradehydro-PGI$_1$ compounds whose preparation and use is described in Ser. No. 821,541, filed Aug. 3, 1977, now U.S. Pat. No. 4,109,082.

The essential material constituting a disclosure of these pyran analogs of 2,3,4,5-tetradehydro-PGI$_1$ compounds is incorporated here by reference from U.S. Pat. No. 4,109,082.

I claim:

1. A prostacyclin analog of the formula

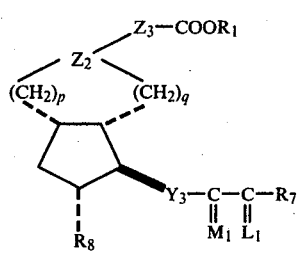

wherein one of p and q is one and the other is zero; wherein Z$_3$ is trans—CH=CH—; wherein Y$_3$ is
(1) trans—CH=CH—,
(2) cis—CH=CH—,
(3) —CH$_2$CH$_2$—, or
(4) —C≡C—,
wherein Z$_2$ is

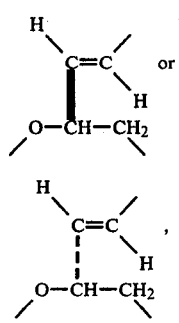

wherein R$_8$ is hydrogen, hydroxy, or hydroxymethyl; wherein M$_1$ is

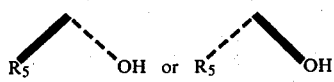

wherein R$_5$ is hydrogen or alkyl with one to 4 carbon atoms, inclusive,
wherein L$_1$ is

or a mixture of

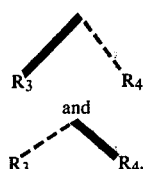
and
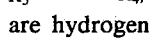

wherein R$_3$ and R$_4$ are hydrogen, methyl, or fluoro, being the same or different, with the proviso that one of R$_3$ and R$_4$ is fluoro only when the other is hydrogen or fluoro;

wherein R$_1$ is hydrogen; alkyl of one to 12 carbon atoms, inclusive; cycloalkyl of 3 to 10 carbon atoms, inclusive; aralkyl of 7 to 12 carbon atoms, inclusive; phenyl; phenyl substituted with one, two, or three chloro or alkyl of one to 3 carbon atoms; phenyl substituted in the para position by

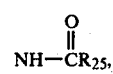 (a)

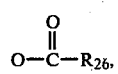 (b)

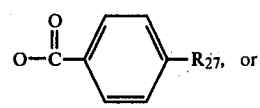 (c)

 (d)

wherein R$_{25}$ is methyl, phenyl, acetamidophenyl, benzamidophenyl, or —NH$_2$; R$_{26}$ is methyl, phenyl, —NH$_2$, or methoxy; and R$_{27}$ is hydrogen or acetamido; phenaycl; phenacyl substituted in the para position by chloro, bromo, phenyl, or benzamido; or a pharmacologically acceptable cation; wherein R$_7$ is (1) —(CH$_2$)$_m$—CH$_3$,

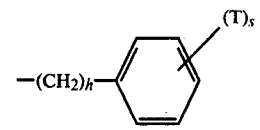 (2)

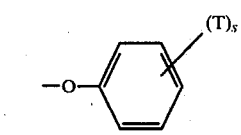 (3)

wherein m is the integer one to 5, inclusive, h is the integer zero to 3, inclusive; s is the integer zero, one, 2, or 3, and T is chloro, fluoro, trifluoromethyl, alkyl of one to 3 carbon atoms, inclusive, with the proviso that not more than two T's are other than alkyl.

2. A prostacyclin analog according to claim 1, wherein p is one.

3. A prostacyclin analog according to claim 2, wherein $R_8$ is hydroxymethyl.

4. (6R)-9,11-Dideoxy-6,9α-epoxymethylene-11-hydroxymethyl-trans,trans-2,3,4,5-tetradehydro-PGF$_1$, a prostacyclin analog according to claim 3.

5. A prostacyclin analog according to claim 2, wherein $R_8$ is hydrogen.

6. (6R)-9,11-Dideoxy-6,9α-epoxymethylene-trans,trans-2,3,4,5-tetradehydro-PGF$_1$, a prostacyclin analog according to claim 5.

7. A prostacyclin analog according to claim 2, wherein $R_8$ is hydroxy.

8. A prostacyclin analog according to claim 7, wherein $Z_2$ is a mixture of

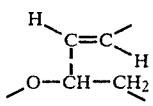

9. (6RS)-9-Deoxy-6,9α-epoxymethylene-trans,trans-2,3,4,5-tetradehydro-PGF$_1$, a prostacyclin analog according to claim 8.

10. A prostacyclin analog according to claim 7, wherein $Z_2$ is

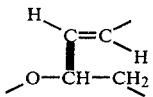

11. (6S)-9-Deoxy-6,9α-epoxymethylene-trans,trans-2,3,4,5-tetradehydro-PGF$_1$, a prostacyclin analog according to claim 10.

12. (6S)-9-Deoxy-6,9α-epoxymethylene-15-methyl-trans,trans-2,3,4,5-tetradehydro-PGF$_1$, a prostacyclin analog according to claim 10.

13. (6S)-9-Deoxy-6,9α-epoxymethylene-16,16-dimethyl-trans,trans-2,3,4,5-tetradehydro-PGF$_1$, a prostacyclin analog according to claim 10.

14. (6S)-9-Deoxy-6,9α-epoxymethylene-16,16-difluoro-trans,trans-2,3,4,5-tetradehydro-PGF$_1$, a prostacyclin analog according to claim 10.

15. A prostacyclin analog according to claim 7, wherein $Z_2$ is

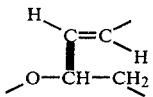

16. A prostacyclin analog according to claim 15, wherein $Y_3$ is cis—CH=CH—.

17. (6R)-9-Deoxy-6,9α-epoxymethylene-cis-13-trans,trans-2,3,4,5-tetradehydro-PGF$_1$, a prostacyclin analog according to claim 16.

18. A prostacyclin analog according to claim 15, wherein $Y_3$ is —C≡C—.

19. (6R)-9-Deoxy-6,9α-epoxymethylene-trans,trans-2,3,4,5,13,14-hexadehydro-PGF$_1$, a prostacyclin analog according to claim 18.

20. A prostacyclin analog according to claim 15, wherein $Y_3$ is —CH$_2$CH$_2$—.

21. (6R)-9-Deoxy-6,9α-epoxymethylene-13,14-dihydro-trans,trans-2,3,4,5-tetradehydro-PGF$_1$, a prostacyclin analog according to claim 20.

22. (6R)-9-Deoxy-6,9α-epoxymethylene-13,14-dihydro-15-methyl-trans,trans-2,3,4,5-tetradehydro-PGF$_1$, a prostacyclin analog according to claim 20.

23. (6R)-9-Deoxy-6,9α-epoxymethylene-13,14-dihydro-16,16-dimethyl-trans,trans,-2,3,4,5-tetradehydro-PGF$_1$, a prostacyclin analog according to claim 20.

24. A prostacyclin analog according to claim 15, wherein $Y_3$ is trans—CH=CH—.

25. A prostacyclin analog according to claim 24, wherein $R_7$ is

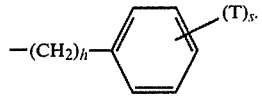

26. A prostacyclin analog according to claim 24, wherein $R_7$ is

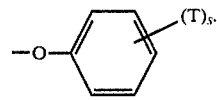

27. A prostacyclin analog according to claim 24, wherein $R_7$ is —(CH$_2$)$_m$—CH$_3$—.

28. A prostacyclin analog according to claim 27, wherein m is 3.

29. A prostacyclin analog according to claim 28, wherein $R_5$ is methyl.

30. (6R)-9-Deoxy-6,9α-epoxymethylene-15-methyl-trans,trans-2,3,4,5-tetradehydro-PGF$_1$, a prostacyclin analog according to claim 29.

31. A prostacyclin analog according to claim 28, wherein $R_5$ is hydrogen.

32. A prostacyclin analog according to claim 31, wherein at least one of $R_3$ and $R_4$ is fluoro.

33. (6R)-9-Deoxy-6,9α-epoxymethylene-16,16-difluoro-trans,trans-2,3,4,5-tetradehydro-PGF$_1$, a prostacyclin analog according to claim 32.

34. A prostacyclin analog according to claim 31, wherein at least one of $R_3$ and $R_4$ is methyl.

35. (6R)-9-Deoxy-6,9α-epoxymethylene-16,16-dimethyl-trans,trans-2,3,4,5-tetradehydro-PGF$_1$, a prostacyclin analog according to claim 34.

36. A prostacyclin analog according to claim 31, wherein $R_3$ and $R_4$ are both hydrogen.

37. (6R)-9-Deoxy-6,9α-epoxymethylene-trans,trans-2,3,4,5-tetradehydro-PGF$_1$, methyl ester, a prostacyclin analog according to claim 36.

38. (6R)-9-Deoxy-6,9α-epoxymethylene-trans,trans-2,3,4,5-tetradehydro-PGF$_1$, tris(hydroxymethyl)amino methane salt, a prostacyclin analog according to claim 36.

39. (6R)-9-Deoxy-6,9α-epoxymethylene-trans,trans-2,3,4,5-tetradehydro-PGF$_1$, adamantanamine salt, a prostacyclin analog according to claim 36.

40. (6R)-9-Deoxy-6,9α-epoxymethylene-trans,trans-2,3,4,5-tetradehydro-PGF$_1$, a prostacyclin analog according to claim 36.

41. A prostacyclin analog according to claim 1, wherein q is one.

42. A prostacyclin analog according to claim 41, wherein $R_8$ is hydroxymethyl.

43. (6R)-9,11-Dideoxy-6,9α-epoxy-7a-homo-11-hydroxymethyl-trans,trans-2,3,4,5-tetradehydro-PGF$_1$, a prostacyclin analog according to claim 42.

44. A prostacyclin analog according to claim 41, wherein $R_8$ is hydrogen.

45. (6R)-9,11-Dideoxy-6,9α-epoxy-7a-homo-trans,-trans-2,3,4,5-tetradehydro-PGF$_1$, a prostacyclin analog according to claim 44.

46. A prostacyclin analog according to claim 41, wherein $R_8$ is hydroxy.

47. A prostacyclin analog according to claim 46, wherein $Z_2$ is a mixture of

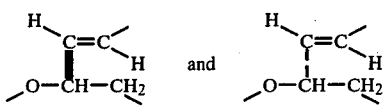

48. (6RS)-9-Deoxy-6,9α-epoxy-7a-homo-trans,trans-2,3,4,5-tetradehydro-PGF$_1$, a prostacyclin analog according to claim 47.

49. A prostacyclin analog according to claim 46, wherein $Z_2$ is

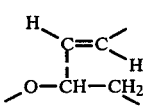

50. (6S)-9-Deoxy-6,9α-epoxy-7a-homo-trans,trans-2,3,4,5-tetradehydro-PGF$_1$, a prostacyclin analog according to claim 49.

51. (6S)-9-Deoxy-6,9α-epoxy-7a-homo-15-methyl-trans,trans-2,3,4,5-tetradehydro-PGF$_1$, a prostacyclin analog according to claim 49.

52. (6S)-9-Deoxy-6,9α-epoxy-7a-homo-16,16-dimethyl-trans,trans-2,3,4,5-tetradehydro-PGF$_1$, a prostacyclin analog according to claim 49.

53. (6S)-9-Deoxy-6,9α-epoxy-7a-homo-16,16-difluoro-trans,trans-2,3,4,5-tetradehydro-PGF$_1$, a prostacyclin analog according to claim 49.

54. A prostacyclin analog according to claim 46, wherein $Z_2$ is

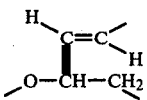

55. A prostacyclin analog according to claim 54, wherein $Y_3$ is cis—CH=CH—.

56. (6R)-9-Deoxy-6,9α-epoxy-7a-homo-cis-13-trans,-trans-2,3,4,5-tetradehydro-PGF$_1$, a prostacyclin analog according to claim 55.

57. A prostacyclin analog according to claim 54, wherein $Y_3$ is —C≡C—.

58. (6R)-9-Deoxy-6,9α-epoxy-7a-homo-trans,trans-2,3,4,5,13,14-hexadehydro-PGF$_1$, a prostacyclin analog according to claim 57.

59. A prostacyclin analog according to claim 54, wherein $Y_3$ is —CH$_2$CH$_2$—.

60. (6R)-9-Deoxy-6,9α-epoxy-7a-homo-13,14-dihydro-trans,trans-2,3,4,5-tetradehydro-PGF$_1$, a prostacyclin analog according to claim 59.

61. (6R)-9-Deoxy-6,9α-epoxy-7a-homo-13,14-dihydro-15-methyl-trans,trans-2,3,4,5-tetradehydro-PGF$_1$, a prostacyclin analog according to claim 59.

62. (6R)-9-Deoxy-6,9α-epoxy-7a-homo-13,14-dihydro-16,16-dimethyl-trans,trans-2,3,4,5-tetradehydro-PGF$_1$, a prostacyclin analog according to claim 59.

63. A prostacyclin analog according to claim 54, wherein $Y_3$ is trans-CH=CH—.

64. A prostacyclin analog according to claim 63, wherein $R_7$ is

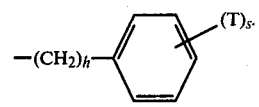

65. A prostacyclin analog according to claim 63, wherein $R_7$ is

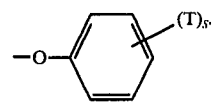

66. A prostacyclin analog according to claim 63, wherein $R_7$ is —(CH$_2$)$_m$—CH$_3$—.

67. A prostacyclin analog according to claim 66, wherein m is 3.

68. A prostacyclin analog according to claim 67, wherein $R_5$ is methyl.

69. (6R)-9-Deoxy-6,9α-epoxy-7a-homo-15-methyl-trans,trans-2,3,4,5-tetradehydro-PGF$_1$, a prostacyclin analog according to claim 68.

70. A prostacyclin analog according to claim 67, wherein $R_5$ is hydrogen.

71. A prostacyclin analog according to claim 70, wherein at least one of $R_3$ and $R_4$ is fluoro.

72. (6R)-9-Deoxy-6,9α-epoxy-7a-homo-16,16-difluoro-trans,trans-2,3,4,5-tetradehydro-PGF$_1$, a prostacyclin analog according to claim 71.

73. A prostacyclin analog accordin to claim 70, wherein at least one of $R_3$ and $R_4$ is methyl.

74. (6R)-9-Deoxy-6,9α-epoxy-7a-homo-16,16-dimethyl-trans,trans-2,3,4,5-tetradehydro-PGF$_1$, a prostacyclin analog according to claim 73.

75. A prostacyclin analog according to claim 70, wherein $R_3$ and $R_4$ are both hydrogen.

76. (6R)-9-Deoxy-6,9α-epoxy-7a-homo-trans,trans-2,3,4,5-tetradehydro-PGF$_1$, methyl ester, a prostacyclin analog according to claim 75.

77. (6R)-9-Deoxy-6,9α-epoxy-7a-homo-trans,trans-2,3,4,5-tetradehydro-PGF$_1$, tris(hydroxymethyl)amino methane salt, a prostacyclin analog according to claim 75.

78. (6R)-9-Deoxy-6,9α-epoxy-7a-homo-trans,trans-2,3,4,5-tetradehydro-PGF$_1$, adamantanamine salt, a prostacyclin analog according to claim 75.

79. (6R)-9-Deoxy-6,9α-epoxy-7a-homo-trans,trans-2,3,4,5-tetradehydro-PGF$_1$, a prostacyclin analog according to claim 75.

* * * * *